(12) United States Patent
Schwartz et al.

(10) Patent No.: US 7,846,181 B2
(45) Date of Patent: *Dec. 7, 2010

(54) SUTURE LOCKING DEVICE

(75) Inventors: Herbert E. Schwartz, Fort Wayne, IN (US); Thomas C. May, Winona Kale, IN (US); Robert-Jan Enzerink, Davis, CA (US); John Margetts, Bountiful, UT (US)

(73) Assignee: DePuy Mitek, Inc., Raynham, MA (US)

( * ) Notice: Subject to any disclaimer, the term of this patent is extended or adjusted under 35 U.S.C. 154(b) by 14 days.

This patent is subject to a terminal disclaimer.

(21) Appl. No.: 11/354,770

(22) Filed: Feb. 15, 2006

(65) Prior Publication Data
US 2006/0135996 A1    Jun. 22, 2006

Related U.S. Application Data

(60) Continuation of application No. 10/186,805, filed on Jul. 1, 2002, now Pat. No. 7,033,380, which is a division of application No. 09/883,691, filed on Jun. 18, 2001, now Pat. No. 6,432,123, which is a division of application No. 09/474,416, filed on Dec. 29, 1999, now Pat. No. 6,319,271.

(60) Provisional application No. 60/114,170, filed on Dec. 30, 1998.

(51) Int. Cl.
*A61B 17/04* (2006.01)
(52) U.S. Cl. .................................... 606/232
(58) Field of Classification Search ........... 606/232, 606/74, 103; 24/115 R, 129 R, 130, 129 W, 24/132 WL, 136 R; 411/2–5
See application file for complete search history.

(56) References Cited

U.S. PATENT DOCUMENTS

| 3,664,345 | A | 5/1972 | Dabbs et al. |
| 3,952,377 | A | 4/1976 | Morell |
| 3,976,079 | A | 8/1976 | Samuels et al. |
| 4,245,374 | A | 1/1981 | Suzuki |
| 4,291,698 | A | 9/1981 | Fuchs et al. |
| 4,455,717 | A | 6/1984 | Gray |
| 4,669,473 | A | 6/1987 | Richards et al. |
| 4,741,330 | A | 5/1988 | Hayhurst |
| 4,750,492 | A | 6/1988 | Jacobs |
| 4,823,794 | A | 4/1989 | Pierce |
| 4,976,715 | A | 12/1990 | Bays et al. |
| RE34,021 | E | 8/1992 | Mueller et al. |

(Continued)

FOREIGN PATENT DOCUMENTS

EP    0632999    6/1994

OTHER PUBLICATIONS

O'Mera, Patrick, "The Basic Science of Meniscus Repair," *Orthopaedic Review*, pp. 681-686, (Jun. 1993).

(Continued)

*Primary Examiner*—Julian W Woo
(74) *Attorney, Agent, or Firm*—Barnes & Thornburg LLP

(57) ABSTRACT

A device for locking a suture in place without the need for tying knots once the suture is placed within tissue is provided. The device comprises an anchor having a cannula and a locking mechanism for securing the suture within the cannula.

3 Claims, 4 Drawing Sheets

U.S. PATENT DOCUMENTS

| | | |
|---|---|---|
| 5,258,015 A | 11/1993 | Li et al. |
| 5,269,809 A | 12/1993 | Hayhurst et al. |
| 5,320,633 A | 6/1994 | Allen et al. |
| 5,383,905 A | 1/1995 | Golds et al. |
| 5,391,173 A | 2/1995 | Wilk |
| 5,520,691 A | 5/1996 | Branch |
| 5,626,614 A | 5/1997 | Hart |
| 5,630,824 A | 5/1997 | Hart |
| 5,725,556 A | 3/1998 | Moser et al. |
| 5,861,004 A | 1/1999 | Kensey et al. |
| 5,899,921 A | 5/1999 | Caspari et al. |
| 5,902,321 A * | 5/1999 | Caspari et al. ............... 606/232 |
| 5,919,208 A | 7/1999 | Valenti |
| 5,954,747 A | 9/1999 | Clark |
| 6,010,525 A | 1/2000 | Bonutti et al. |
| 6,066,160 A | 5/2000 | Colvin et al. |
| 6,126,677 A | 10/2000 | Ganaja et al. |
| 6,200,329 B1 | 3/2001 | Fung et al. |
| 6,306,159 B1 | 10/2001 | Schwartz et al. |
| 7,033,380 B2 * | 4/2006 | Schwartz et al. ............ 606/232 |

OTHER PUBLICATIONS

Clearfix Screw Advertisement, *Innovasive Devices, Inc.*, (1998).
Winters and Justin, "Clearfix Meniscal Screw," *Innovative Devices, Inc.* (1998).
Surgical Dynamics, Meniscal Stapler Advertisement, (1997).
Bionix Implants, Meniscus Arrow Advertisement, (1996).
Instrument Makar, Inc., Meniscus Mender II Advertisement, (1989).
William G. Clancy, Jr., M.D., and Ben K. Graf, M.D., "Arthroscopic Meniscal Repair," *ACUFEX Microsurgical, Inc. Advertisement*, (1988).

* cited by examiner

SUTURE LOCKING DEVICE

This application is a continuation of U.S. patent application Ser. No. 10/186,805, filed Jul. 1, 2002 now U.S. Pat. No. 7,033,380, which is a divisional of U.S. patent application Ser. No. 09/883,691, filed Jun. 18, 2001 now U.S. Pat. No. 6,432,123, which is a divisional of U.S. patent application No. 09/474,416, filed Dec. 29, 1999 now U.S. Pat. No. 6,319,271, which claims priority under 35 U.S.C. §119(e) to U.S. Provisional Application No. 60/114,170, filed Dec. 30, 1998, which is expressly incorporated by reference herein.

FIELD OF THE INVENTION

The present invention relates to a device for locking a suture in vivo, more particularly to a device for locking a suture in vivo without the need for tying knots once the suture is placed within tissue. The present invention also relates to a method for using such a device to approximate tissue and to lock the suture in place.

BACKGROUND AND SUMMARY OF THE INVENTION

It is known in the art to approximate damaged or torn tissue by use of a suture. In many instances, the suture is looped through tissue, and the two ends are then secured together. Prior art methods for securing a suture include tying knots. Other methods include providing a filament having various protruding portions and securing the filament against one of those protruding portions. See, e.g., U.S. Pat. No. 5,520,691, incorporated herein by reference. Still other prior art methods include compressing the suture between a cylinder/piston wall interface. See, e.g., U.S. Pat. No. 5,630,824, incorporated herein by reference. Such sutures may be used to approximate damage in soft tissue or to attach soft tissue to bone.

The present invention provides a suture locking device that relies on frictional forces. In one embodiment, a suture is passed through an anchor having a tapered or stepped cannula. The suture is then passed through tissue, may be passed through or around a second anchor located on the opposite side of the defect, and looped back through the cannula. One end of the suture may be provided with a knot or bead. As the surgeon pulls on the second end, the knot or bead enters the cannula, pulls the two anchors toward each other, then both strands wedge tightly in the cannula. In an alternative embodiment, instead of a knot or bead, a slip knot is provided on the first end. The second end may be threaded through the slip knot. Again, as the surgeon pulls on the second end, the knot will enter the tapered or stepped cannula, pull the two anchors together, and wedge both strands tightly within the cannula.

In another embodiment of this invention, a locking ring is used to secure the sutures to the anchor. The anchor may be provided with a split section and the suture would pass through this split section. The locking ring may be of either the push-type or the pull-type, and when engaged, the locking ring would force the portions of the split section together, thus wedging the split section together and locking the suture strands in place. The split section may be provided with teeth to grip the suture better.

In another embodiment, the suture may be secured with a snap groove provided on the anchor. As with the locking ring arrangement, the anchor would be provided with a split section. A tooth on one section is sized and shaped to mate with a groove on the other section. When the tooth is snapped into the groove, the suture strands would be locked into place.

An additional embodiment may employ a wedge design. In such a design, the anchor may be provided with a cylindrical cannula, and a wedge would be provided to fit tightly within the cannula. The wedge itself may be partially cannulated to aid in insertion, but the suture would also, in part, pass along the exterior of the wedge, so that frictional forces would secure the suture between the wedge and the inside of the cannula, in order to lock the suture in place.

Alternatively, the suture locking device may comprise laminated sheets. Slits in the laminated sheets would allow the suture to pass in one direction with little resistance. However, the sheets would be designed to lock on the suture when the suture is pulled in the reverse direction. Thus, the surgeon could pull on the suture to tighten it, and the suture would remain locked in place.

Some embodiments of the present invention are described for situations in which the suture is looped through tissue, and two ends of the suture must be secured. Other embodiments are described in which each end of the suture strand is secured independently. It will be understood that the invention may be employed in situations involving a single strand or with multiple suture or filament strands. Also, it will be understood that the scope of this invention is not limited specifically to securing two ends of a suture within one locking mechanism.

The anchor may be made of biocompatible material such as stainless steel, titanium, cobalt chrome, and polyethylene. Preferably, biodegradable materials may also be used, including poly lactic acid and poly lactic-glycolic acid. Other biodegradable materials are known. See, e.g., U.S. Pat. No. 4,976,715, hereby incorporated by reference. The suture may be made of resorbable or non-resorbable material, as are known in the art.

Therefore, in one embodiment of the present invention, a device is provided for locking a suture in place, the device comprising an anchor having a cannula, the cannula for receiving a suture, and a locking mechanism for locking the suture in place. The locking mechanism may comprise a bead, knot, or wedge sized to wedge within the cannula or the locking mechanism may comprise a locking ring. The cannula may be cylindrical, tapered, or stepped.

In another embodiment of the present invention, a device is provided for locking a suture in place, the device comprising an anchor having a cannula and a locking mechanism. The cannula is for receiving the suture, and the locking mechanism is for locking the suture within the cannula. The locking mechanism may comprise a locking ring or a snap groove.

In still another embodiment of the present invention, a device for locking a suture in place is provided, comprising an anchor having a front edge and a rear edge, the anchor having a cannula extending from the front section to the rear section, and a locking mechanism. In this embodiment, the suture comprises a first end and a second end, the suture extending through the cannula of the anchor from the rear edge to the front edge, through a portion of tissue, and extending back through the cannula from the front edge to the rear edge, the second end protruding from the rear edge of the suture. The locking mechanism comprises a bead located at the first end of the suture, and the bead sized to fit snugly within a portion of the cannula. Pulling the second end of the suture causes the bead to travel toward the front edge of the anchor and to wedge within the portion of the cannula, thereby locking the suture in place.

Additional features of the present invention will become apparent to those skilled in the art upon consideration of the following detailed description of preferred embodiments exemplifying the best mode of carrying out the invention as presently perceived.

DETAILED DESCRIPTION OF THE DRAWINGS

Figure 1:
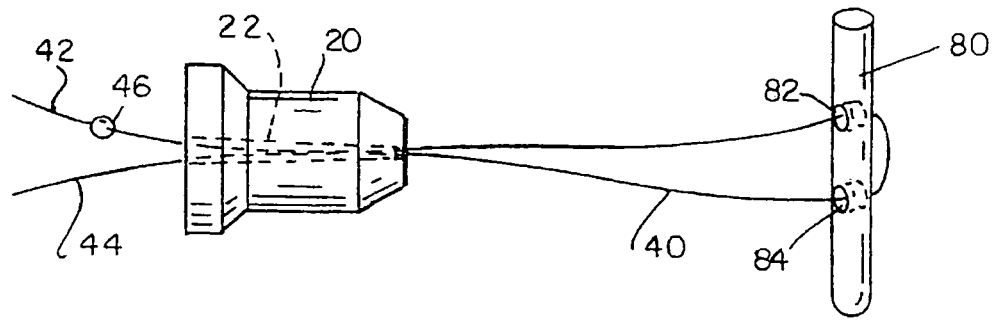
FIG. 1 is a cross-sectional view of a locking device of this invention, in which the locking device comprises an anchor with a tapered cannula and a suture with a bead, shown in combination with a second anchor.

FIG. 1 shows generally a suture locking device of this invention in a combination as the device may be employed. In the illustrative embodiment, a suture 40 passes through a cannula 22 in an anchor 20. The suture loops through or around a second anchor 80, and then returns through cannula 22. In use, anchor 20 and second anchor 80 may be located on opposite sides of a soft tissue defect (not shown), and suture 40 may be used to pull the defect together. Alternatively, second anchor 80 may be located within or beyond a portion of bone (not shown), and anchor 20 may be used to attach soft tissue to the bone. Other applications are also possible.

As shown, second anchor 80 is provided with two holes 82, 84. Suture 40 extends from first anchor 20 to second anchor 80, loops through first hole 82 and returns through second hole 84 back to first anchor 20. Alternatively, second anchor 80 may be provided with one hole through which suture 40 passes before returning to first anchor 20. In other embodiments, second anchor 80 may be provided with a singular cannulation lengthwise with the suture 40 extending therethrough, or the second anchor 80 may be provided without any holes, and the suture 40 may merely loop over second anchor 80. In some situations, a second anchor may not be necessary, and suture 40 simply loops over or through tissue.

In the embodiment shown in FIG. 1, the anchor 20 is configured to bury partially or totally into tissue, for use in tissue repair where interference with the tissue surface is not desirable. This configuration may be desirable for use on surfaces such as the inner surface of the meniscus of the knee, where a protruding anchor may interfere with joint articulation. However, as illustrated in FIGS. 10-13, anchors which are configured to abut, without entering, tissue are also within the scope of this invention. The combination illustrated in FIG. 1 is meant merely as an example of a suture/anchor combination that may be locked with the suture locking device of this invention.

Referring still to FIG. 1, suture 40 is provided with a first end 42 and a second end 44. As shown, first end 42 is provided with a bead 46, and the cannula 22 is tapered. As the surgeon pulls on the second end 44 of suture 40, the bead 46 enters the cannula 22. With continued pulling, the bead 46 pulls anchor 20 toward second anchor 80, for example, to close a defect in tissue or to secure soft tissue to a bone. When anchor 20 is fully seated, bead 46 wedges into cannula 22, and bead 46 secures second end 44 within the cannula 22.

Figure 2:
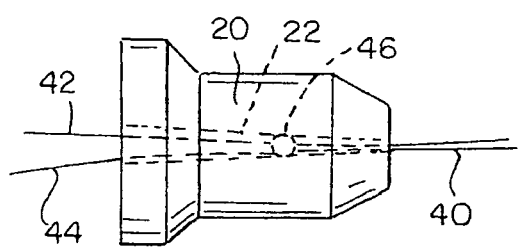
FIG. 2 is a cross-sectional view of the anchor of FIG. 1, with the suture in locked position.
Figure 3:
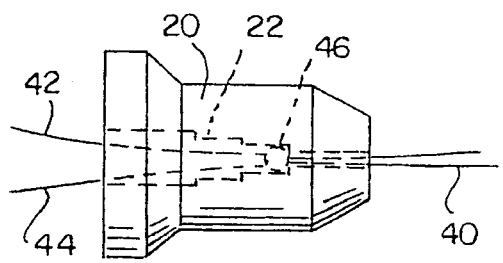
FIG. 3 is similar to FIG. 2, except that the cannula is stepped rather than tapered.

FIG. 2 illustrates the anchor 20 of FIG. 1 after the suture 40 has been pulled tight and locked into place. FIG. 3 illustrates an alternative embodiment wherein the cannula 22 is stepped, rather than tapered. As with the embodiment illustrated in FIG. 2, when suture 40 is pulled tight, the bead 46 locks the suture 40 in place. Bead 46 may be permanently affixed to suture 40 in any number of ways, as are known in the art. Alternatively, suture 40 may be manufactured with bead 46 as a protuberance integral with the suture filament. Also, bead 46 may be a knot in suture 40 of sufficient size to lock suture 40 in place.

Figure 4:
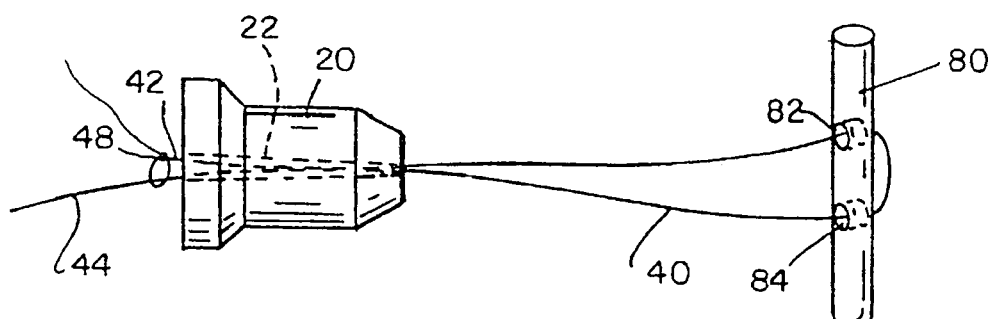
FIG. 4 is similar to FIG. 1, except that a slip knot replaces the bead.

Another embodiment is illustrated in FIG. 4. The first end 42 of suture 40 is provided with a slip knot 48. As with the embodiment shown in FIG. 1, the anchor 20 is provided with a cannula 22 that may be tapered or stepped. Preferably, second end 44 is fed through loop 49 of slip knot 48, and the loop 49 may be tensioned slightly. As the surgeon pulls on the second end 44, slip knot 48 will travel distally along the second end 44, until slip knot 48 begins to push the anchor 20 toward the second anchor 80. As with the bead 46 of FIG. 1, slip knot 48 wedges in cannula 22, locking the suture in place.

Figure 5:
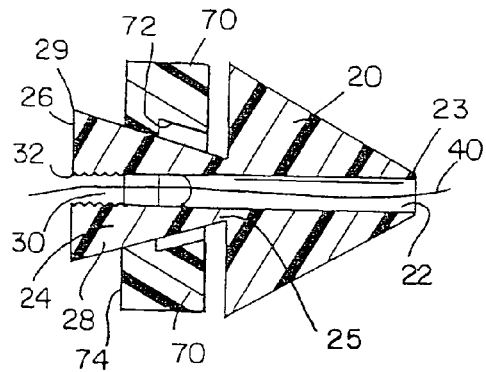
FIG. 5 is a cross-sectional view of another embodiment of this invention, in which the suture locking device comprises a pull locking ring in combination with a cannulated anchor.
Figure 6:
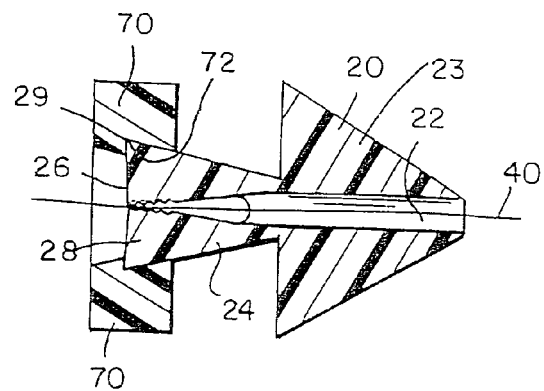
FIG. 6 is similar to FIG. 5, except showing the device in a locked position.

FIGS. 5-8 relate to embodiments employing locking rings. FIGS. 5 and 6 involve a pull locking ring with FIG. 5 illustrating the open position and FIG. 6 illustrating the locked position. As illustrated in FIGS. 5 and 6, anchor 20 is provided with cannula 22. Preferably, rear section 24 of anchor 20 is split into first and second rear portions 26, 28, to define split gap 30. An annular locking ring 70 is provided around middle section 25. Once anchor 20 and suture 40 are properly positioned, locking ring 70 may be pulled in the direction away from front 23 and toward rear 24 of anchor 20. First and second rear portions 26, 28 are compressed together by locking ring 70, thus securing suture 40 within. Teeth 32 may be provided to insure secure gripping of suture 40. As illustrated in FIG. 6, a groove 72 on locking ring 70 may be provided for seating on tip 29, to secure locking ring 70 in place.

Referring specifically to FIG. 5, as illustrated, in the open position locking ring 70 sits between front section 23 and rear section 24. An insertion tool (not shown) may engage a recess or protuberance (not shown) in rear surface 74 of the locking ring 70, in order to aid in pulling locking ring 70 to the closed position, as illustrated in FIG. 6. Also, because middle section 25 of anchor 20 provides a recess in which locking ring 70 sits while in the open position, locking ring 70 need not be physically connected to anchor 20. Alternatively, a frangible portion (not shown) may be used to secure locking ring 70 to anchor 20. The frangible portion would be broken as locking ring 70 is pulled back to the closed position.

Figure 7:
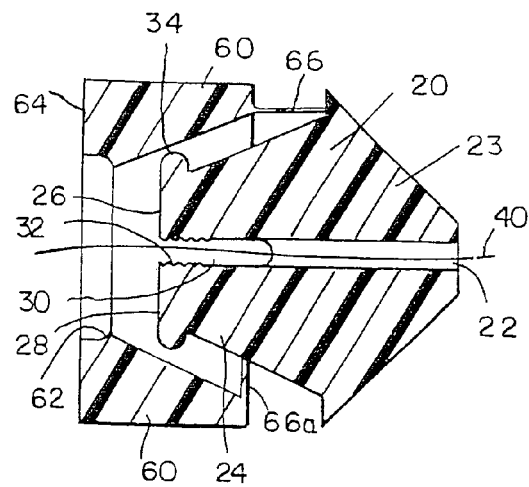
FIG. 7 is similar to FIG. 5, except showing a device with a push locking ring.
Figure 8:
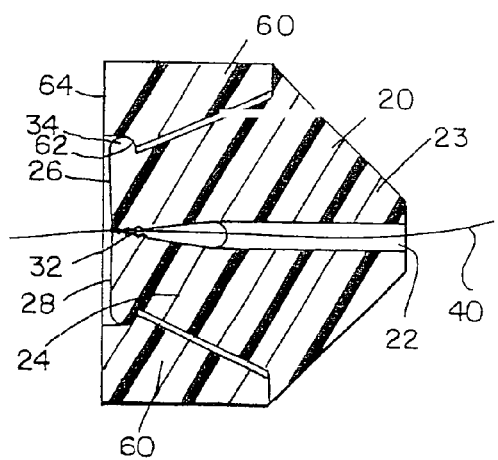
FIG. 8 is similar to FIG. 7, except showing the device in a locked position.

FIGS. 7 and 8 illustrate an embodiment of a suture locking device employing a push locking ring. FIG. 7 illustrates the push locking ring 60 with the device in the open position. As with the embodiment shown in FIGS. 5 and 6, anchor 20 may be provided with a rear section 24 which has been split into first and second rear portions 26, 28, defining slit gap 30. A locking ring 60 is disposed around rear section 24. When locking ring 60 is pushed toward the front section 23 of anchor 20, the locking ring compresses rear portions 26 and 28 together, locking suture 40 therebetween. As with the pull locking ring embodiment illustrated in FIGS. 5 and 6, the anchor 20 may be provided with teeth 32, in order to better secure suture 40. Once locking ring 60 is in the locked position, lip 34 may be provided to lock edge 62 in place and restrain locking ring 60 from moving back to the open position. As illustrated, edge 62 is recessed from rear surface 64. However, edge 62 may protrude from or be contiguous with rear surface 64.

Still referring to FIGS. 7 and 8, rear surface 64 of locking ring 60 may be provided with a recess (not shown) for use with an insertion tool (not shown). Also, locking ring 60 may be connected to anchor 20 by a frangible portion 66. When force is placed on locking ring 60, the frangible portion 66 would break, and locking ring 60 would slip into the locked position shown in FIG. 8. An alternative location for the frangible portion is illustrated as frangible portion 66a, although many other locations are possible. Alternatively, locking ring 60 may be connected by a tether (not shown). In still another alternative embodiment, locking ring 60 need not be physically connected to anchor 20, and locking ring 60 may be inserted simply by pushing it along suture 40.

Figure 9:
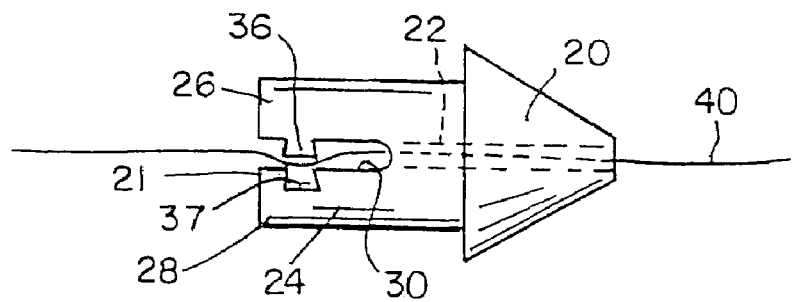
FIG. 9 is a cross-sectional view of an embodiment of this invention employing a snap lock design.

FIG. 9 illustrates an embodiment of this invention which employs a snap groove. As with the locking ring embodiments, rear section 24 of anchor 20 is split into first and second portions 26, 28, defining split groove 30. A tooth 36 is provided on first portion 26, while a matching groove 37 is provided on second portion 28. Suture 40, which has been inserted through cannula 22, also extends between tooth 36 and grove 37. When tooth 36 is snapped into groove 37, suture 40 is captured therebetween and becomes locked into place. It is understood that, while a singular tooth and groove are illustrated in FIG. 9, embodiments employing multiple teeth and grooves are within the scope of this invention.

Figure 10:
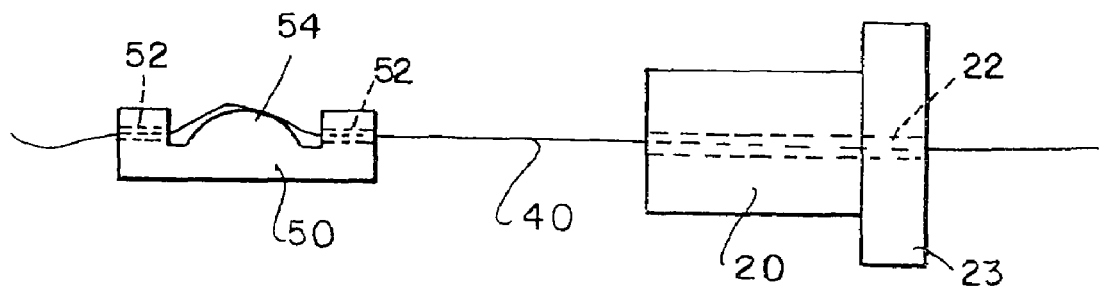
FIG. 10 is a cross-sectional view of still another embodiment of this invention which employs a wedge design.

A wedge design may be used, as illustrated in FIG. 10. In this embodiment, anchor 20 is provided with cannula 22. A wedge 50 is shaped to fit snugly within cannula 22. Wedge 50 may be partially cannulated, as illustrated with cannulae 52. As illustrated, suture 40 may be threaded through cannula 22 of anchor 20 and then through cannulae 52 of wedge 50. As illustrated, suture 40 also passes over arch 54. With tension on suture 40, wedge 50 may be pushed into cannula 22. Suture 40 then becomes locked between arch 54 and the inner wall of cannula 22. While the illustrated cannula 22 and wedge 50 are cylindrical, it will be understood that other shapes may be used. It is also understood that cannulae 52 are provided only for ease of insertion, and that wedge 50 may be provided without cannulations.

Still referring to FIG. 10, the anchor 20 as illustrated may be used in applications where front section 23 of anchor 20 is to remain flush with the tissue surface. However, it is understood that a wedge suture locking device may be used in various applications with various anchor designs.

Figure 11:
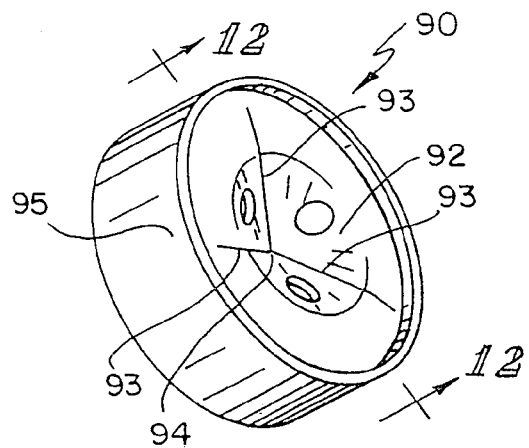
FIG. 11 is a perspective view of an additional embodiment of this invention, employing a laminated sheet design.
Figure 12:
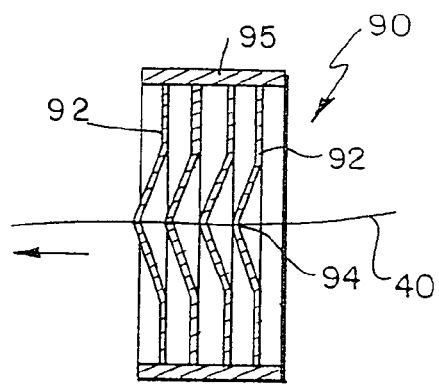
FIG. 12 is a cross-sectional view of FIG. 11, along line 12-12.

FIGS. 11-12 illustrate another embodiment of a locking device of this invention. Locking ring 90 is constructed from a series of laminated sheets 92. The laminated sheets may be bonded or welded together along the circumference 95 of locking ring 90. Slits 93 may be provided through each of the laminated sheets 92. An aperture 94 is defined as the intersection of slits 93. Aperture 94 allows suture 40 to pass through locking ring 90. As can be seen in FIG. 12, the laminated sheets are constructed such that if suture 40 is pulled in the direction indicated by the arrow, suture 40 may pass freely with little resistance. However, if suture 40 is pulled in the opposite direction, slits 93 close as laminated sheets 92 start bending back upon themselves. Thus, suture 40 is locked into position.

Figure 13:
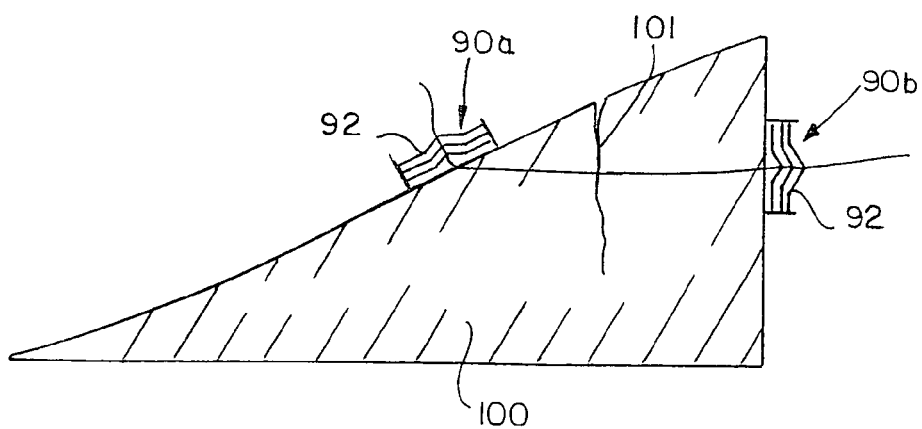
FIG. 13 is a cross-sectional view of a meniscus of a knee, showing a defect approximated by a suture that is locked into position by using two locking devices of FIG. 11.

FIG. 13 illustrates two locking rings of FIGS. 11 and 12 used to repair a defect 101 in a meniscus 100. As illustrated, locking ring 90a is located at the inner surface 102 of meniscus 100, while locking ring 90b is located at the outer surface 103 of meniscus 100. Locking rings 90a and 90b secure suture 40 in place, thereby approximating the defect 101. It should be understood that FIG. 13 is illustrative of just one example of the present invention. Any of the embodiments could be used to approximate such a defect. The various embodiments of this invention may be used to secure one or multiple sutures in a wide variety of uses.

Although the invention has been described in detail with reference to certain preferred embodiments, variations and modifications exist within the scope and spirit of the invention as described and defined in the following claims.

The invention claimed is:

1. A device for locking a suture in place, comprising:
   an anchor having a front section and a rear section, a cannula extending through the front and rear sections for extending the suture therethrough, the rear section including a first rear portion and a second rear portion, and
   a push locking ring sized to receive the rear section of the anchor therein and compress the first rear portion and the second rear portion to lock the suture therebetween within the cannula, wherein the push locking ring is connected to the anchor by a frangible portion that is broken upon movement of the push locking ring toward the anchor.

2. A device for locking a suture in place, comprising:
   an anchor having a front section and a rear section, a cannula extending through the front and rear sections for extending the suture therethrough, the rear section including a first rear portion and a second rear portion, and
   a push locking ring configured to receive the rear section of the anchor therein and compress the first rear portion and the second rear portion to lock the suture therebetween, wherein the push locking ring is connected to the anchor by a frangible portion that is broken when the push lock ring is placed in a locked position and said rear section of the anchor comprises a lip recessed from the rear section surface and positioned to contact an edge of the push locking ring when the push locking ring is placed in a locked position thereby restraining the push locking ring.

3. A device for locking a suture in place, comprising:
   an anchor having a front section and a rear section, a cannula extending through the front and rear sections for extending the suture therethrough, the rear section including a first rear portion and a second rear portion, and
   a push locking ring sized to receive the rear section of the anchor therein and compress the first rear portion and the second rear portion to lock the suture therebetween, wherein the push locking ring is connected to the anchor by a frangible portion that is broken when the push locking ring is placed into a locked position.

* * * * *